United States Patent
Verri et al.

(10) Patent No.: US 7,351,344 B2
(45) Date of Patent: Apr. 1, 2008

(54) STERILE SYSTEM AND METHOD FOR FILTERING BIOLOGICAL OR MEDICAL LIQUIDS, ESPECIALLY BLOOD OR BLOOD CONSTITUENTS

(75) Inventors: Paolo Verri, Concordia (IT); Giorgio Mari, Mirandola (IT)

(73) Assignee: Fresenius Hemocare Italia S.R.L., Modena (IT)

( * ) Notice: Subject to any disclaimer, the term of this patent is extended or adjusted under 35 U.S.C. 154(b) by 145 days.

(21) Appl. No.: 10/503,105

(22) PCT Filed: Jan. 9, 2003

(86) PCT No.: PCT/EP03/00127

§ 371 (c)(1),
(2), (4) Date: Jul. 29, 2004

(87) PCT Pub. No.: WO03/064000

PCT Pub. Date: Aug. 7, 2003

(65) Prior Publication Data

US 2005/0082218 A1     Apr. 21, 2005

(30) Foreign Application Priority Data

Jan. 29, 2002   (IT)   ............. TO2002A0080

(51) Int. Cl.
*B01D 37/00*     (2006.01)
*B01D 35/00*     (2006.01)
*B01D 35/01*     (2006.01)

(52) U.S. Cl. ............... 210/767; 210/120; 210/136; 210/252; 210/257.1; 210/258; 210/436; 210/472; 604/408; 604/410

(58) Field of Classification Search ............... 210/120, 210/136, 252, 257.1, 258, 436, 472, 767; 604/408, 410
See application file for complete search history.

(56) References Cited

U.S. PATENT DOCUMENTS 5,545,339 A * 8/1996 Bormann et al. .......... 210/806
5,601,730 A   2/1997 Page et al.

(Continued)

FOREIGN PATENT DOCUMENTS

DE      197 33 407      2/1999

(Continued)

OTHER PUBLICATIONS

English translation of European Patent No. 0 888 789 A1.*

*Primary Examiner*—John Kim
(74) *Attorney, Agent, or Firm*—Kenyon & Kenyon LLP

(57) ABSTRACT

The invention relates to a sterile system and a method for filtering biological or medical liquids, especially blood or blood constituents. According to the filtering system and method, the sterile air already in the system is collected before the beginning of the filtration process, and after the filtration process, in order to completely empty the system used. Said filtering system comprises a collapsible container having a first and second air inlet/outlet line. The first air inlet/outlet line communicates with the first chamber of the filter by means of a flow connection, and the second air inlet/outlet line with the second chamber of the filter. Only the air inlet/outlet line communicating with the first filter chamber is sealed by a hydrophobic membrane or a return valve in the filtering system, such that the system has an especially simple structure.

20 Claims, 2 Drawing Sheets

U.S. PATENT DOCUMENTS 5,776,338 A * 7/1998 Mari .......................... 210/252

FOREIGN PATENT DOCUMENTS

| EP | 0 642 801 | | 4/1998 |
|---|---|---|---|
| EP | 0 888 789 | * | 1/1999 |
| GB | 2211755 A | * | 7/1989 |
| WO | WO 91/17809 | | 11/1991 |

* cited by examiner

STERILE SYSTEM AND METHOD FOR FILTERING BIOLOGICAL OR MEDICAL LIQUIDS, ESPECIALLY BLOOD OR BLOOD CONSTITUENTS

FIELD OF THE INVENTION

The invention relates to a sterile system for the filtration of biological or medical fluids, in particular of blood or blood components, as well as a method for the filtration of biological or medical fluids.

BACKGROUND OF THE INVENTION

There is known from EP 0 642 801 A1 a filtration device, which includes a collecting bag and a flexible-tube line system with a filter. The bag, which contains the fluid to be filtered, is not a component of the device. The flexible-tube line system of the known filtering device has, apart from the flexible-tube line into which the filter is connected, also a bypass line with a non-return valve, which branches off from the flexible-tube line upstream and downstream of the filter, so that after the end of the filtration process air can flow out of the collecting bag into the bag containing the fluid to be filtered. The exit-side chamber of the filter has an additional aeration opening, which is connected via a flexible-tube line with a drip chamber, which is connected into the flexible-tube line section leading to the filter.

A filtering system for biological or medical fluids is also known from WO 91/17809. The fluid to be filtered is transferred under the influence of gravity from a receiving bag via a flexible-tube line and a filter into a collecting bag. The drawback is that fluid still remains in the flexible-tube line and the filter after the end of the filtration process, i.e. after the fluid has ceased to flow into the collecting bag. In order to recover this fluid, there is provided on the flexible-tube line a gas inlet upstream of the filter and a gas outlet downstream of the filter. After the end of the filtration process, gas is conveyed into the system via the inlet, said gas displacing the liquid in the system as it is conveyed away again via the outlet.

In a preferred form of embodiment of the filtering system known from WO 91/17809, it is proposed, for the purpose of completely emptying the system, to provide on the flexible-tube line an outlet line upstream of the filter and a de-aeration line downstream of the filter. The aeration and de-aeration line lead into a common aeration and de-aeration bag, whereby hydrophobic membranes on both lines prevent fluid from flowing into the container. The filtering system is based on the principle that air is fed from the container via the outlet line to the system for the purpose of aerating the system and air is fed from the system via the de-aeration line to the container for the purpose of de-aerating the system. The connection points are therefore also designated as gas inlet and outlet.

EP 0 888 789 A1 describes a sterile system for the filtering of blood and blood components, which also makes use of a collapsible container, in which the air in the system is collected before the filtration process is started and used for the complete emptying of the system after the end of the filtration process. The filter of the known filtering system connected into the collecting line has two chambers, whereof the first chamber is connected to the collapsible container via a first flexible-tube line and the second chamber is connected to the collapsible container via a second flexible-tube line. Both flexible-tube lines are closed with a hydrophobic membrane. The fluid to be filtered flows into the collecting container thereby displacing the air in the two filter chambers through both flexible-tube lines into the collapsible container. For complete emptying of the system, the second flexible-tube line is first closed, whereby air flows from the collapsible container via the first flexible-tube line into the first chamber of the filter. The second flexible-tube line is then opened again, so that air flows via the second flexible-tube line into the second chamber of the filter. The effect of this is that the first filter chamber is aerated first and then the second filter chamber.

The known filtering system has been tried and tested in practice. The use of two sterile filters, which increase production costs, has however proved to be a drawback.

SUMMARY OF THE INVENTION

The problem underlying the invention, therefore, is to provide a system for the filtration of biological or medical fluids, in particular of blood or blood components, that is easy to handle and easy to produce, said system being able to be completely emptied without air having to be fed to the system from outside causing the sterility of the system to be lost. A further problem underlying the invention is to provide a method for the filtration of biological or medical fluids that can be implemented with simple means, said method permitting the complete transfer of the fluid from one container into another container via a filter under sterile conditions.

The solution to these problems takes place according to the present invention.

With the filtering system and method according to the invention, the sterile air already present in the system is collected before the start of the filtration process, i.e. before the flow connection to the collecting container is cleared, and is used to completely empty the system after the end of the filtration process, i.e. when the fluid has ceased to flow into the collecting container.

The filtering system according to the invention is characterised in that only one of the two air inlet or outlet lines is closed by a non-return valve or a hydrophobic membrane. While the fluid is flowing via the collecting line into the collecting container, the second air inlet or outlet of the collecting container is closed. Only for the complete emptying of the system is the second air inlet or outlet opened. The air in the collapsible container flows on the one hand via the first air inlet or outlet line into the first chamber of the filter, whereby the non-return valve or the hydrophobic membrane clears a passage for the air, and on the other hand from the collapsible container via the second air inlet or outlet line into the second filter chamber, so that the second chamber is also emptied.

An air inlet or outlet line is understood to mean all means with which air can be fed to the collapsible container or air can be conveyed away from the container. The air inlet or outlet line can also include an opening in the container or a connection piece or a piece of the flexible-tube line formed on the container, i.e. the non-return valve or the hydrophobic membrane can also be integrated into the collapsible container.

A hydrophobic membrane closing the air inlet or outlet line is understood to mean all means which permit a supply of air into and out of the air inlet or outlet line, but which prevent a flow of fluid. The hydrophobic membrane can be arranged inside or outside the collapsible container, e.g. the hydrophobic membrane can be arranged in a piece of the flexible-tube line leading to the air inlet or outlet. A non-return valve in place of a hydrophobic membrane as another embodiment of the present invention permits a passage of fluid only in the direction of the first filter chamber, but not into the collapsible container.

A particularly rapid complete emptying of the system is achieved when the second air inlet or outlet line emerges into the second chamber at a side lying opposite the outlet of the second filter chamber, because then air can flow from the collapsible container from above into the filter chamber and simultaneously fluid can flow away from below out of the second chamber.

The first air inlet or outlet line can branch off from the first collecting line and be connected directly to the first filter chamber.

The collapsible container is preferably formed as a flexible plastic bag, which is welded with the air inlet or outlet lines. For the purpose of fixing, the plastic bag can be provided with a clip, through which the first collecting line extends. It is however also possible for the collapsible container to be formed directly on the filter.

The first collecting line can be connected directly to a container containing the fluid to be filtered. It is however also possible for the collecting line to be connected to the container by a connector system. Such sterile connection devices are generally known.

In a further preferred embodiment of the present invention, the filter is a filter for the removal of leucocytes. The filter can however also be a filter for the removal of other blood components from full blood or other components from other biological or medical fluids.

DETAILED DESCRIPTION

An exemplary of embodiment of the invention is explained in greater detail below by reference to the drawings.

Figure 1:
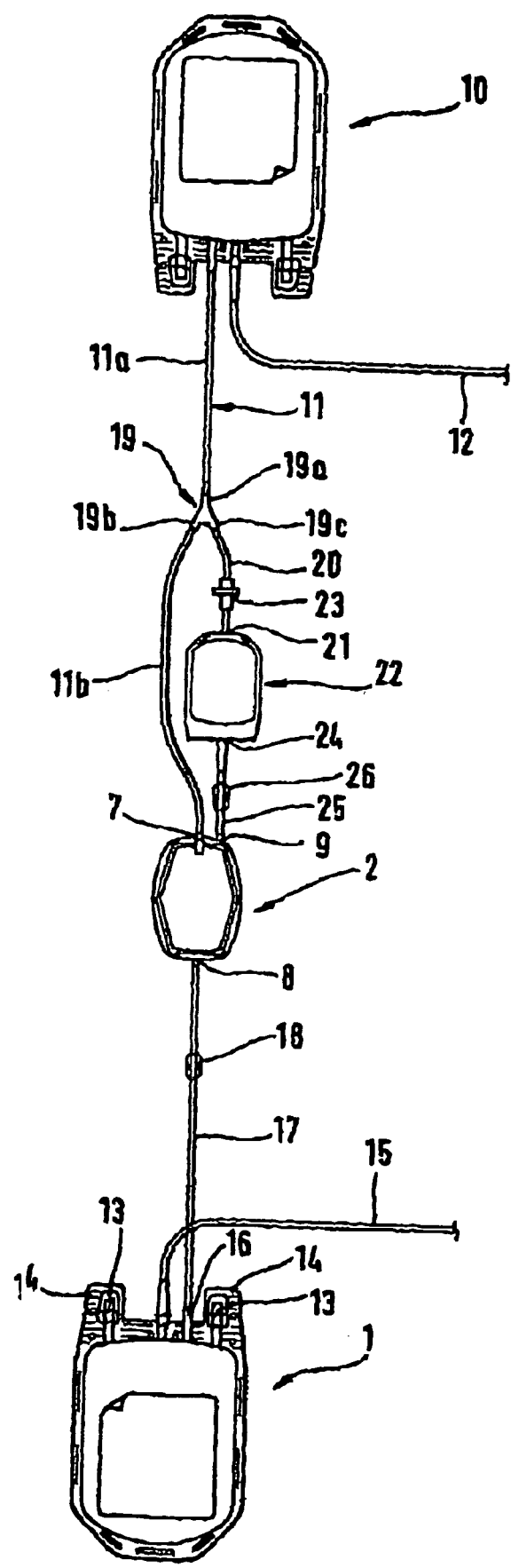
FIG. 1 shows a diagrammatic representation of a preferred embodiment of a filtering system according to the present invention.

FIG. 1 shows a preferred embodiment of the filtering system of the present invention in plan view. The filtering system includes a collecting container 1 for accommodating the filtered fluid, for example a leucocyte-free thrombocyte concentrate, and a filter 2 for removing a blood component, for example a leucocyte filter.

Figure 2:
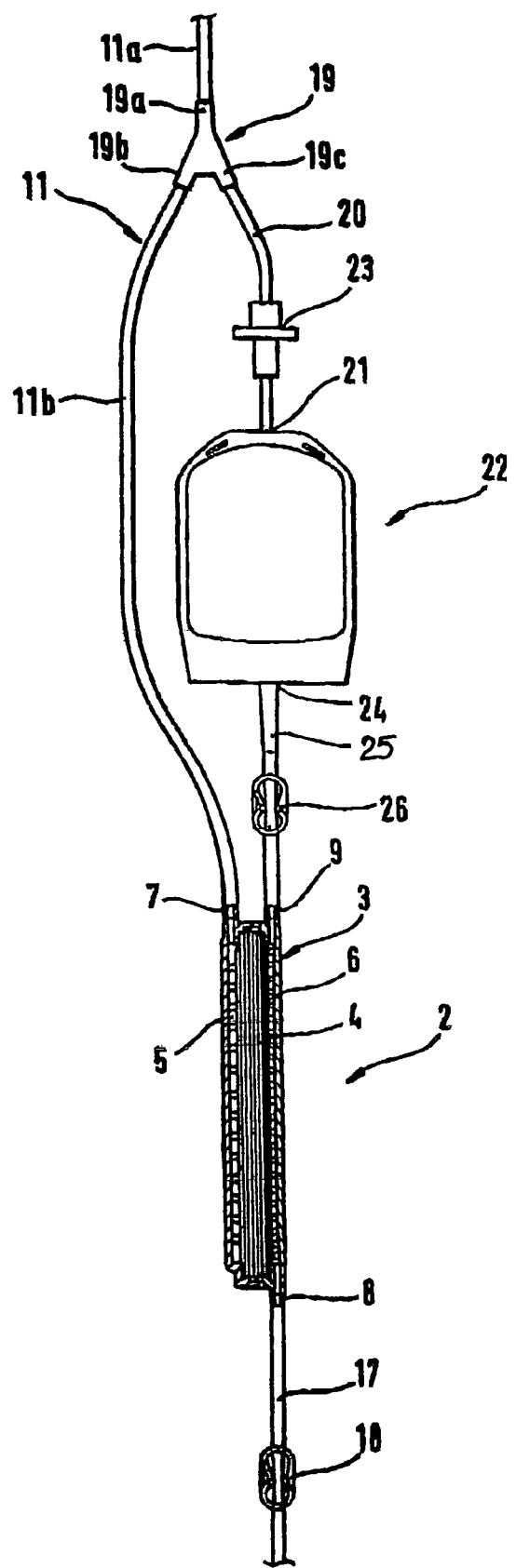
FIG. 2 shows an enlarged representation of a partial view of the filtering system depicted in FIG. 1.

The side view of filter 2 is shown in FIG. 2 in enlarged representation. The filter has a flat housing 3, which is divided by a filter material 4 into a first and second filter chamber 5, 6, respectively. First filter chamber 5 has an inlet 7 at the upper housing edge and second filter chamber 6 has an outlet 8 at the lower housing edge and an air-inlet or aeration connection 9 at the upper housing edge.

The fluid to be filtered, for example a thrombocyte concentrate, is made ready in a receiving container 10, in particular in a flexible plastic bag, which consists of two plastic films welded together at their edges and which is connected to the filtering system. Connected to receiving container 10 is a first collecting line 11 in the form of a flexible-tube line, which leads to inlet 7 of filter 2. Collecting line 11 is connected to the receiving container in a sterile manner by means of the known connection devices. Apart from first collecting line 11, FIG. 1 also shows a further flexible-tube line 12, which can be used for the supply of blood or a blood component into the receiving container.

Collecting container 1 is also a flexible plastic bag. Two connection pieces 13 sealed with membranes capable of being pierced are welded onto the other edge of the plastic bag, said connection pieces each being sealed in a sterile manner by means of tear-open tabs 14. Connection pieces 13 can be used for example to remove a leucocyte-free thrombocyte concentrate by means of suitable spike connectors.

FIG. 1 also shows a further flexible-tube 15, which leads away from collecting container 1. This flexible-tube line can be used for the removal of a blood component.

Collecting container 1 has an inlet 16, which is connected to outlet 8 of second filter chamber 6 of filter 2 via a second collecting line 17 again in the form of a flexible-tube line. A first flexible-tube clamp 18 is provided on the line for the purpose of opening and closing second collecting line 17.

First collecting line 11 has a first section 11a, which leads to common connection piece 19a of a branch element 19, whilst a second section 11b of first collecting line 11 departs from a branch piece 19b of branch element 19 and leads to inlet 7 of first chamber 5 of filter 2. Departing from the other branch piece 19c of branch element 19 is a first air inlet or outlet line 20, which leads to a first air inlet or outlet 21 of a collapsible container 22 in the form of a flexible plastic bag. The end of the flexible-tube line is rigidly welded with the upper edge of the plastic bag. Before air inlet or outlet 21 of collapsible container 22, there sits on first air inlet or outlet line 20 an intermediate piece 23 with a hydrophobic membrane, i.e. gas-permeable membrane which however is impermeable for liquids, which seals air inlet or outlet 21. In place of a hydrophobic membrane, however, the intermediate piece can also contain a non-return valve, which is permeable for fluid in the direction of the first collecting line, but is impermeable in the direction of the collapsible container.

Departing from a first air inlet or outlet 24 of collapsible container 22 is a second air inlet or outlet line 25, which leads to air-inlet or aeration connection 9 of second chamber 6 of filter 2. The upper end of second air inlet or outlet line 25 is rigidly welded with the lower edge of collapsible container 22. For the purpose of opening and closing second air inlet or outlet line 25, a second flexible-tube clamp 26 is provided which sits on the flexible-tube line.

Collapsible container 22 has a volume which corresponds approximately to the volume of the two filter chambers 5, 6 of filter 2 including the adjacent flexible-tube lines. The volume of the collapsible container should not however be smaller than the volume of the filter together with the adjacent lines, because otherwise complete emptying of the filtering system is not ensured.

The method according to the present invention for the filtering of fluids using the filtering system will be described in detail below.

Flexible-tube clamp 18 of second collecting line 17 is first closed and second flexible-tube clamp 26 on second air inlet or outlet line 25 is opened. It is assumed here that receiving container 10 has already been connected to first collecting line 11 of the filtering system.

Under the influence of gravity, the concentrate flows from receiving container 10 into filter 2 thereby displacing the enclosed air through second air inlet or outlet line 25 into collapsible container 22. The volume of collapsible container 22 is dimensioned in such a way that first collecting line 11, the two filter chambers 5, 6 of filter, 2 and the section of second collecting line 17 upstream of first flexible-tube clamp 18 are filled with the fluid to be filtered, whereby the displaced air remains in collapsible container 22, i.e. container 22 does not fill with fluid. Since first air inlet or outlet 21 of container 22 is closed by hydrophobic membrane 23 or non-return valve 23, the air enclosed in the container cannot rise upwards and escape. On the other hand, however, liquid cannot flow into container 22 via first air inlet or outlet line 20.

After an equilibrium state has been established, second flexible-tube clamp 26 is closed and first flexible-tube clamp 18 is opened. The fluid to be filtered now flows out of receiving container 10 via first and second collecting line 11, 17 into collecting container 1. When the fluid flow has come to a standstill, second flexible-tube clamp 26 is again opened, so that air is abruptly sucked into filter 2 from collapsible container 22 via first air inlet or outlet line 20 and second section 11b of first collecting line 11. Since the air collected in collapsible container 22 now flows via first air inlet or outlet line 20 and first collecting line 11 into first chamber 5 of filter 2, first filter chamber 5 is completely emptied without manual intervention being required. Second filter chamber is then emptied, whilst air flows out of container 22 via second air inlet or outlet line 25 from above into the second filter chamber and residual fluid flows downwards out of the second chamber via second collecting line 17.

The invention claimed is:

1. A sterile system for the filtration of fluid, the system comprising:
    a filter including a housing, wherein the housing is divided by a filter material into a first chamber and a second chamber, wherein the first chamber includes a first chamber inlet and the second chamber includes an aeration connection and a second chamber outlet;
    a first collecting line for the feeding of fluid to be filtered, the first collecting line being connected to the first chamber inlet;
    a collecting container including a collecting container inlet;
    a second collecting line which connects the second chamber outlet to the collecting container inlet;
    a means for opening or closing the second collecting line;
    a collapsible container including a first air inlet or outlet line and a second air inlet or outlet line, wherein the first air inlet or outlet line is fluidly connected to the first chamber inlet of the first chamber, and the second air inlet or outlet line is fluidly connected to the aeration connection of the second chamber; and
    a means for opening or closing the second air inlet or outlet line;
    wherein the first air inlet or outlet line is closed by a hydrophobic membrane or a non-return valve that allows a passage of fluid only out of the collapsible container;
    wherein the second air inlet or outlet line does not include a hydrophobic membrane; and
    wherein the volume of the collapsible container is dimensioned such that when the first collecting line, the first chamber, the second chamber, and the section of the second collecting line upstream of the means for opening or closing the second collecting line are filled with the fluid to be filtered, the displaced air remains in the collapsible container.

2. The sterile system according to claim 1, wherein the second air inlet or outlet line fluidly connects to the second chamber at a point opposite from the second chamber outlet.

3. The sterile system according to claim 1, wherein the collapsible container is a flexible plastic bag.

4. The sterile system according to claim 1, wherein the first air inlet or outlet line branches off from the first collecting line.

5. The sterile system according to claim 1, wherein the means for opening or closing the second collecting line and the means for opening or closing the second air inlet or outlet line are flexible-tube clamps.

6. The sterile system according to claim 1, wherein the filter is a leucocyte filter.

7. The sterile system according to claim 2, wherein the collapsible container is a flexible plastic bag.

8. The sterile system according to claim 7, wherein the first air inlet or outlet line branches off from the first collecting line.

9. The sterile system according to claim 8, wherein the means for opening or closing the second collecting line and the means for opening or closing the second air inlet or outlet line are flexible-tube clamps.

10. The sterile system according to claim 9, wherein the filter is a leucocyte filter.

11. A method for the filtration of a fluid with a sterile filtering system comprising a filter including a housing, wherein the housing is divided by a filter material into a first chamber and a second chamber, wherein the first chamber includes a first chamber inlet and the second chamber includes an aeration connection and a second chamber outlet;
    a first collecting line for the feeding of fluid to be filtered, the first collecting line being connected to the first chamber inlet;
    a collecting container including a collecting container inlet;
    a second collecting line which connects the second chamber outlet to the collecting container inlet;
    a means for opening or closing the second collecting line;
    a collapsible container including a first air inlet or outlet line and a second air inlet or outlet line, wherein the first air inlet or outlet line is fluidly connected to the first chamber inlet of the first chamber, and the second air inlet or outlet line is fluidly connected to the aeration connection of the second chamber; and
    a means for opening or closing the second air inlet or outlet line;
    wherein the first air inlet or outlet line is closed by a hydrophobic membrane or a non-return valve that allows a passage of fluid only out of the collapsible container;
    wherein the second air inlet or outlet line does not include a hydrophobic membrane; and
    wherein the volume of the collapsible container is dimensioned such that when the first collecting line, the first chamber, the second chamber, and the section of the second collecting line upstream of the means for opening or closing the second collecting line are filled with the fluid to be filtered, the displaced air remains in the collapsible container; the method comprising:
    closing the means for opening or closing the second collecting line, and opening the means for opening or closing the second air inlet or outlet line;
    conveying the fluid to be filtered through the first collecting line, the first chamber, the filter material and into the second chamber, thereby displacing air into the collapsible container;
    closing the means for opening or closing the second air inlet or outlet line, and opening the means for opening or closing the second collecting line;

conveying the fluid through the first collecting line, the first chamber, the filter material, the second chamber, the second collecting line, and into the collecting container; and opening the means for opening or closing the second air inlet or outlet line, such that the air collected in the collapsible container is conveyed back into the second chamber via the second air inlet or outlet line.

12. The method according to claim 11, wherein the second air inlet or outlet line fluidly connects to the second chamber at a point opposite from the second chamber outlet.

13. The method according to claim 11, wherein the collapsible container is a flexible plastic bag.

14. The method according to claim 11, wherein the first air inlet or outlet line branches off from the first collecting line.

15. The method according to claim 11, wherein the means for opening or closing the second collecting line and the means for opening or closing the second air inlet or outlet line are flexible-tube clamps.

16. The method according to claim 11, wherein the filter is a leucocyte filter.

17. The method according to claim 12, wherein the collapsible container is a flexible plastic bag.

18. The method according to claim 17, wherein the first air inlet or outlet line branches off from the first collecting line.

19. The method according to claim 18, wherein the means for opening or closing the second collecting line and the means for opening or closing the second air inlet or outlet line are flexible-tube clamps.

20. The method according to claim 19, wherein the filter is a leucocyte filter.

* * * * *